US006921392B1

(12) United States Patent
Drevik et al.

(10) Patent No.: US 6,921,392 B1
(45) Date of Patent: Jul. 26, 2005

(54) ABSORBENT PRODUCT WITH ARCUATE LONGSIDES OF END PORTION

(75) Inventors: Solgun Drevik, Molnlycke (SE); Gunnar Castmo, Vastra Frolunda (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/856,299

(22) PCT Filed: Nov. 15, 1999

(86) PCT No.: PCT/SE99/02086

§ 371 (c)(1),
(2), (4) Date: Aug. 13, 2001

(87) PCT Pub. No.: WO00/30585

PCT Pub. Date: Jun. 2, 2000

(30) Foreign Application Priority Data

Nov. 20, 1998 (SE) .............................. 9803981

(51) Int. Cl.⁷ .............................................. A61F 13/15
(52) U.S. Cl. ............................ 604/385.01; 604/385.04; 604/385.05; 604/386
(58) Field of Search ...................... 604/385.01, 385.04, 604/386, 385.05

(56) References Cited

U.S. PATENT DOCUMENTS

| 4,806,411 A | | 2/1989 | Mattingly, III et al. |
|---|---|---|---|
| 5,358,500 A | | 10/1994 | Lavon et al. |
| D366,524 S | * | 1/1996 | Chung ........................ D24/125 |
| 5,713,886 A | | 2/1998 | Sturino |
| D392,736 S | * | 3/1998 | Erickson .................... D24/125 |
| 5,729,835 A | | 3/1998 | Williams |

FOREIGN PATENT DOCUMENTS

| DE | 299 03 391 | 6/1999 |
|---|---|---|
| TW | 280765 | 7/1996 |
| WO | WO 97/39713 | 10/1997 |

* cited by examiner

Primary Examiner—John J. Calvert
Assistant Examiner—Jacqueline Stephens
(74) Attorney, Agent, or Firm—Young & Thompson

(57) ABSTRACT

Absorbent product (1), such as a sanitary towel, incontinence protection or protection for briefs, which product has an essentially elongate shape with a longitudinal direction (8) and a transverse direction (9), an upper side (10) and a lower side (11), and has a first end portion (6) intended to face forwards on the wearer and a second end portion (7) intended to face backwards on the wearer, which product is characterized in that the width of the second end portion (7) of the product is 40 mm maximum, and in that the long sides (2, 3) of this end portion (7) are essentially arcuate.

8 Claims, 2 Drawing Sheets

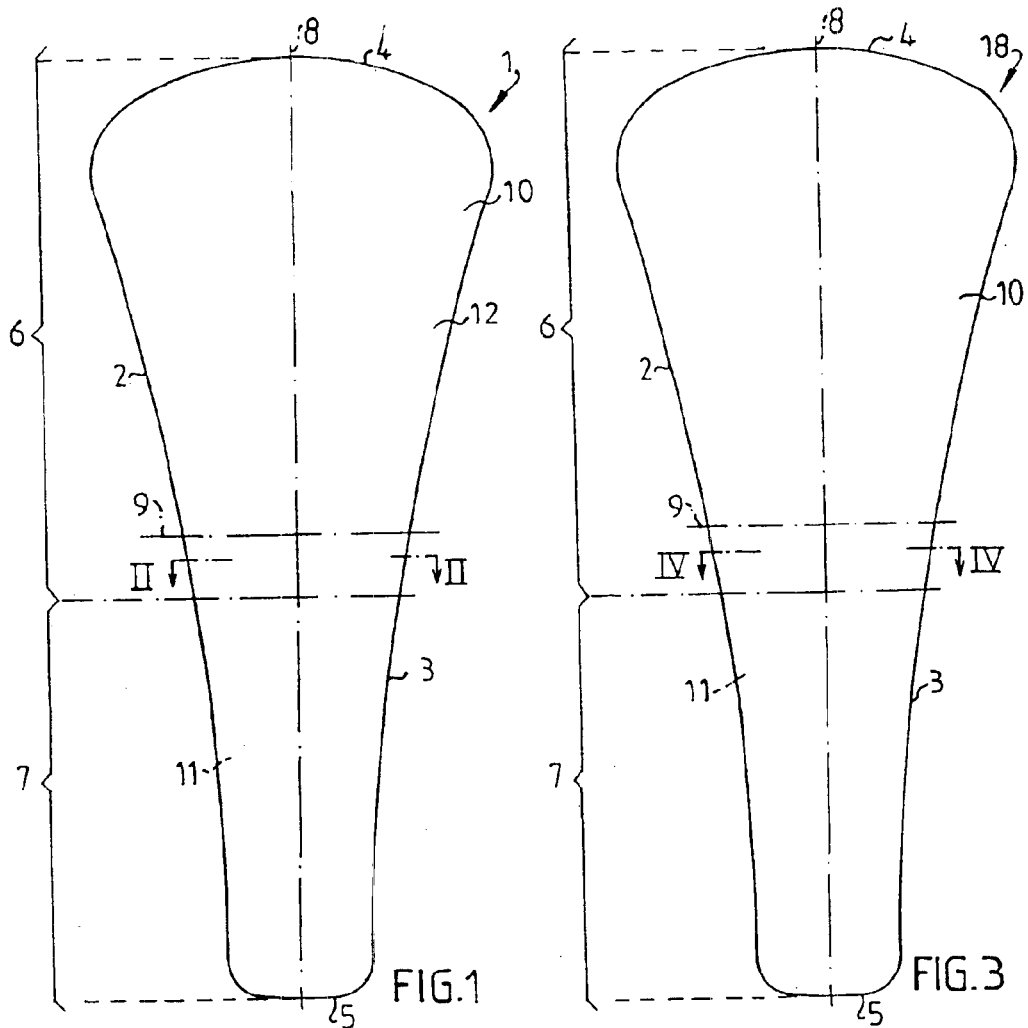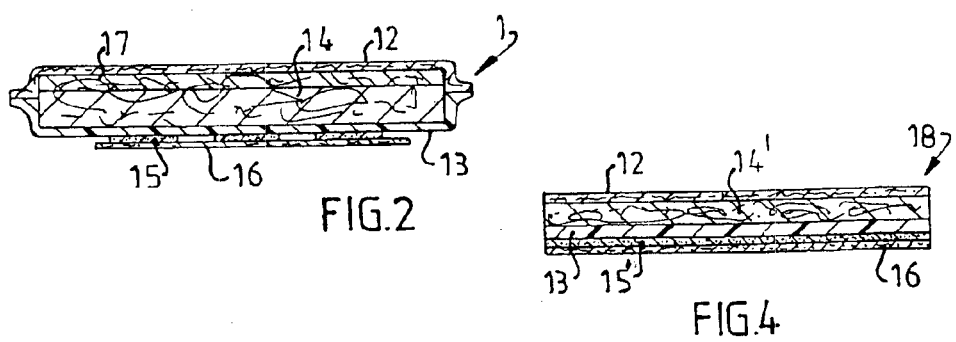

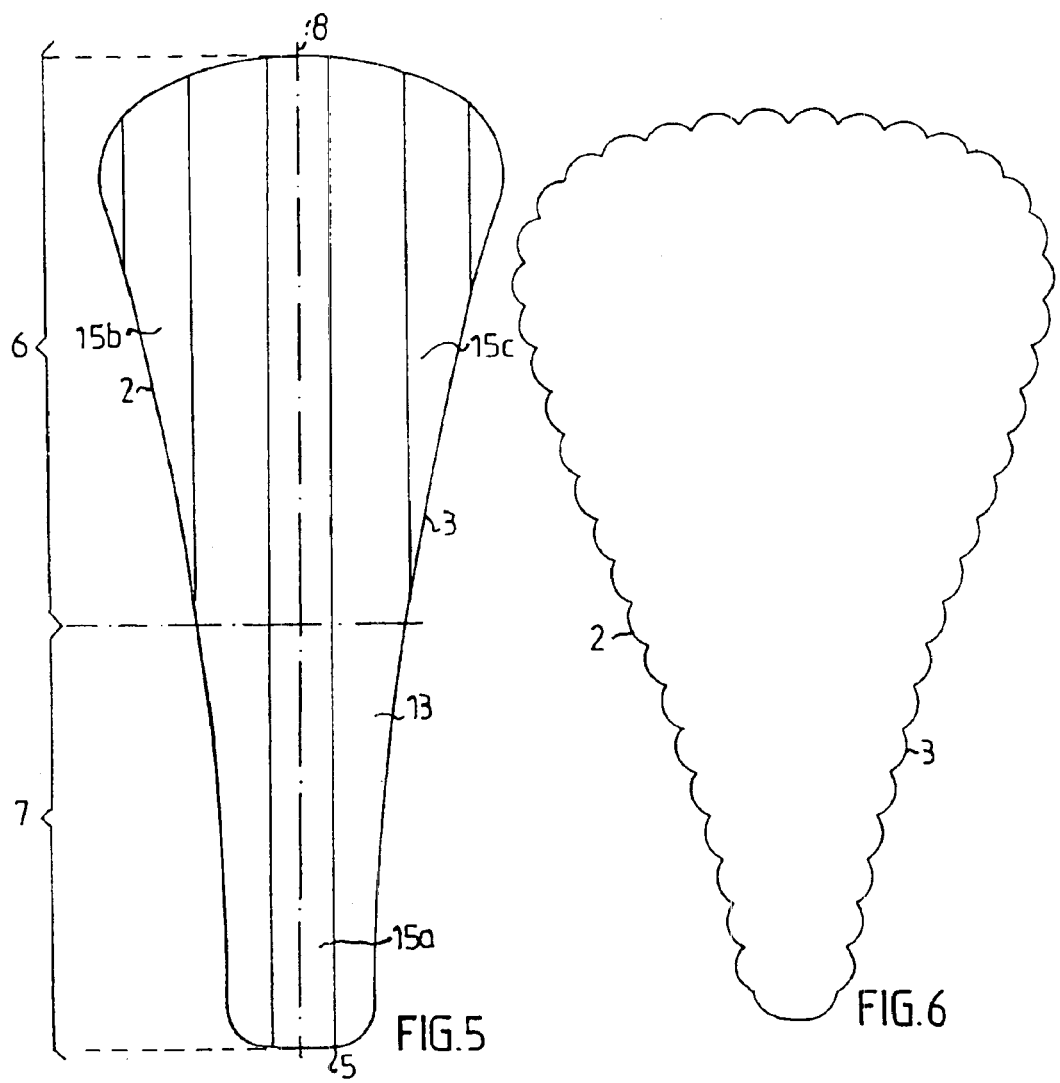
FIG.5
FIG.6
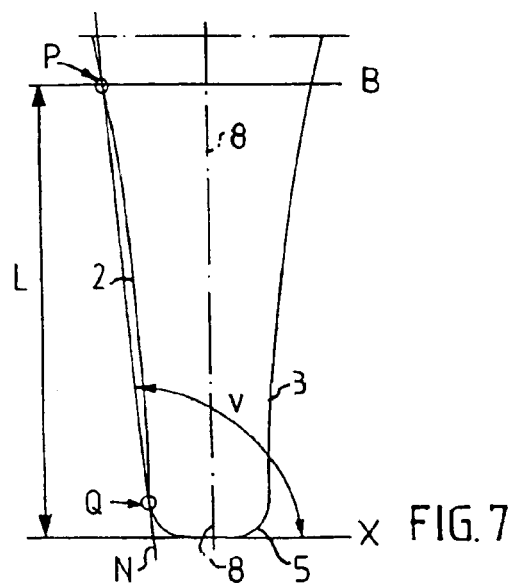
FIG.7

ABSORBENT PRODUCT WITH ARCUATE LONGSIDES OF END PORTION

FIELD OF TECHNOLOGY

Absorbent product such as a sanity towel incontinence protection or protection for briefs, which product has an essentially elongate shape with a longitudinal direction and a transverse direction, an upper side and a lower side, and has a first end portion intended to face forwards on the wearer and a second end portion intended to face backwards on the wearer.

BACKGROUND

Conventional abs ent products of the above-mentioned types usually have a rectangular or hour-glass appearance.

One problem associated with these shapes of absorbent product is the increasing use of string briefs. A product of rectangular hour-glass form will protrude beyond the edges of the string briefs and spoil somewhat the elegance which is the whole point of wearing this type of underwear. The alternative is to make the product sufficiently narrow so that the entire product width will be contained within the conies of the narrowest part of the string briefs. The absorption capacity of a product made in this way will however be very limited.

It has therefore been proposed to design the absorbent products with a narrower part and a wider part. See for example U.S. Pat. No. 5,713,886, U.S. Pat. No. 5,729,835 and WO 97/39713.

WO97/39713 describes a sanitary towel with one end having a tapered three-dimensional form, and a second plane end with a straight form. One problem connected with the sanitary towel described in WO97/39713 is that no guidance is provided as to the dimensions required to make this a discreet product. Another problem with a product according to WO97/39713 is that the absorbent product has an end with straight form, which is also unsatisfactory from the discretion point of view.

OBJECT OF THE INVENTION

The object of the invention is to overcome the above-mentioned problem and make an absorbent product which will be discreet even when used with string briefs.

SHORT DESCRIPTION OF THE INVENTION

A product of the type described in the introduction, with which the problem associated with previously known similar products has been for the most part avoided, is according to the invention characterized in that the width of the second end portion of the product is 40 mm maximum, and in that the long sides of this end portion are essentially arcuate.

According to a preferred embodiment, the width of the second end portion is between 15 and 40 mm. According to another preferred embodiment, the width of the second end portion is 18–30 mm.

To be suitable for use with string briefs with open-work front, the product length is advantageously 150 mm or less.

DESCRIPTION OF THE INVENTION

According to the invention, the above-mentioned problem will be solved by making the absorbent product with one portion so arranged that the product will not be visible from the outside when used with a pair of string briefs.

Surprisingly it has been shown that the crutch width is fairly similar on most string briefs. Measurements show that a product width not exceeding 40 mm is sufficiently narrow to be concealed by the briefs.

The width will preferably lie between 15 and 40 mm.

As mentioned earlier, the absorption capacity would not normally be sufficient in the case of a product with such small width, where the width does not vary. It is therefore important for the absorbent product to follow the edge of the brief so that the available absorption surface will be as large as possible.

A product which is as wide as possible is also important from the leakage point of view. The risk of leakage from the side of the briefs, as well as soiling of the briefs, is reduced if the product shape follows that of the briefs. The absorbent product according to the invention therefore has, at least in part, arcuate long sides which follow the shape of the briefs in the crutch area. The long sides of the product do not need to have a smooth arc shape, but it is sufficient that the long sides be essentially arcuate. When we say that the long sides should be essentially arcuate, they could for example also be undulated but where the undulations essentially follow an arc. Other forms for the long sides of the product are of course also possible as long as the longitudinal side edges of the product have essentially arc shape.

Studies of the crutch section of string briefs show that certain designs of the arc shape on the long sides of the product are particularly favourable. This favourable shape can be expressed in that the radius of curvature of an imagined circle which includes one of the long sides of the product lies within certain determined values. This assumes that the arc can be inscribed in a circle, but a suitable arc shape could also be inscribed in an ellipse. One way of specifying a suitable art shape, which would be valid irrespective of which geometrical figure could incorporate the arc, is to express an angle formed by virtue of the long side of the product being curved. The angle is calculated as that formed by a line running in the transverse direction and tangent to the shortest short side of the product and a line which intersects or touches one of the long sides of the product at the points where the arc either changes direction or turns into a short side. The value of the angle so formed should lie within certain predetermined limits. The most favourable angle lies between 95° and 110°; see below for a detailed description of the measurement method.

It has been found that it is not necessary for the whole product to be of a determined, very narrow width since the front part of most string briefs on the market is wide enough to accommodate a product of normal width with the long sides of fairly arbitrary shape. This means then that the part of the product which is worn at the front can be designed more freely, according to the absorption capacity requirement which may exist.

It follows then that only one of the end portions—that portion worn at the rear and fitting into the narrow part of the string briefs—needs to be made with a maximum width and a special contour on the long sides. This part lengthwise in the product is referred to below as the rear or second end portion. That part lengthwise in the product which can be designed with a greater degree of freedom will be referred to as the front or first end portion. The two end portions do not necessarily split the product into two parts of equal length. The first end portion is suitably 60–170 mm long, whilst the second end portion is suitably 30–90 mm long. The complete length of the product lies between 140 and 260 mm.

SHORT DESCRIPTION OF THE FIGURES

The invention will be described below in more detail with reference to the exemplary embodiments shown on the drawings.

FIG. 1 shows a plan view of a sanitary towel according to the invention.

FIG. 2 shows a section along line II—II through the sanitary towel in FIG. 1.

FIG. 3 shows a plan view of protection for briefs according to the invention.

FIG. 4 shows a section along line IV—IV through the protection for briefs in FIG. 3.

FIG. 5 shows protection for briefs according to an alternative embodiment of the invention, viewed from below.

FIG. 6 shows a part of a product for protection of briefs according to an alternative embodiment of the invention.

FIG. 7 shows how the extent of the curvature on the long sides of the product can be indicated.

DETAILED DESCRIPTION OF FIGURES AND EMBODIMENTS

FIGS. 1 and 2 show a sanitary towel 1 according to one embodiment of the invention.

Sanitary towel 1 has a basically elongate shape with a longitudinal direction and a transverse direction. It has two long sides 2 and 3, two short sides 4 and 5, a first 6 and a second 7 end portion, a longitudinal centre line 8 extending over the product length and a transverse centre line 9 running laterally over the product width. The longitudinal centre line is considered to be a line extending in the longitudinal direction of the sanitary towel equidistant from the long sides of the product. In the same way, the transverse centre line is a line arranged in the transverse direction of the towel equidistant between the short sides of the towel. Towel 1 has an upper side 10, intended to be turned towards the wearer during use, and a lower side 11 to be turned away from the wearer during use.

Sanitary towel 1 incorporates a liquid-permeable outer layer 12 fixed on the side of the product to be turned towards the wearer (upper side 10) during use, and an impermeable rear layer 13 on the side of the towel which will be turned away from the wearer (lower side 11) during use. Between the outer layer 12 and the impermeable rear layer 13 is an absorption body 14. The outer layer and the rear layer are connected at a joint outside the absorption body.

FIG. 2 shows a section through the towel 1 in FIG. 1 along line II—II. On the lower side 11 of the towel, on its impermeable layer 13, are placed the fasteners in the form of strips 15 made of pressure-sensitive adhesive arranged parallel with the longitudinal centre line 8 of the towel. A removable protective layer 16 is laid on top of adhesive 15. Protective layer 16 is removed by the wearer before the towel is placed in the underwear. Other fastening methods can of course be used, such as Velcro® or friction-fastening.

Outer material 12 could be of any conventional material, for example non-woven, perforated plastic film or a laminate of these two materials.

The most suitable material for the absorption body 14 is cellulose pulp. This can be made available as rolls, bales or sheets which, for the production of sanitary towels, are dry-defibred and converted in fluffed form to a pulp matting, sometimes with an admixture of "superabsorbents" which are polymers with the power to absorb several times their own weight of water or body fluids. One alternative to this is to dry-form pulp matting as described in WO 94/10956. Examples of other usable absorption materials are various types of natural fibre such as cotton fibre, peat or similar. It is of course possible to use absorbent synthetic fibres, or mixtures of natural and synthetic fibres. Absorption body 14 can also include other material such as form stabilizes, fluid-spreading means, or binders such as thermoplastic fibres which have been heat-treated to combine short fibres and particles into a continuous materials. Various types of absorbent foam material can also be used in the absorption body.

The impermeable layer 13 (rear layer) consists of a liquid-impermeable material. Thin, fluid-tight plastic films are suitable for this purpose, but it is also possible to use material which is naturally permeable, but which is provided with a coating of plastic, resin or other fluid-tight material. In this way leakage of fluid from the lower side of the absorbent product is prevented. The impermeable layer 13 can therefore be made of any material which fulfills the impermeability criterion and offers sufficient flexibility and skin tolerance for this purpose. Examples of material suitable for use as an impermeable layer are plastic films, non-woven and laminates of these two. Plastic films can for instance be of polyethylene, polypropylene or polyester. The impermeable layer can alternatively consist of a laminate of an impermeable plastic layer, turned towards the absorption body, and a non-woven layer turned towards the underwear of the wearer. This type of construction provides a leakage safe barrier layer with textile feel.

Between the outer layer 12 and the absorption body 14 is an acquisition layer 17. The purpose of this layer 17 is to draw fluid into the towel and transit it down to absorption body 14. This acquisition layer 17 can for example be a non-woven material of low density.

It can be seen from FIG. 1 that the long sides 2 and 3 of the sanitary towel are essentially arcuate. The arc shape is designed so that these long sides 2, 3 curve inwards towards the longitudinal centre line 8. The first end portion 6 has a width of 65 mm at its widest part. The widest part of the second end portion 7 is 30 mm.

FIGS. 3 and 4 show a product 18 for protection of briefs according to one embodiment of the invention. There is an outer layer 12, a barrier layer 13 and an absorption body 14. The absorption body can be an "airlaid", i.e. an airlaid cellulose body. The outer layer 12 and barrier layer 13 can be constructed of the same material as described for the same layers 12 and 13 of the sanitary towel shown in FIGS. 1–2.

FIG. 4 shows a section along line IV—IV through the protection for briefs in FIG. 3. On the lower side II of this product, on its impermeable layer 13, is a fastener in the form of a layer 15', of pressure-sensitive adhesive covering the whole surface. Over this adhesive layer 15', is a removable protective layer 16 which will be removed by the wearer before the product is placed in the underwear. Other fixing methods such as Velcro® or friction-fastening can of course be used.

It can be seen from FIG. 3 that the outer contour of the protection for briefs is similar to that of the sanitary towel 1 shown in FIG. 1. The first end portion 6 has a maximum width of 60 mm, whilst the maximum width of the second end portion 7 is 22 mm.

FIG. 5 shows a product for protection of briefs according to an alternative embodiment of the invention. What distinguishes this product from that described in FIG. 34 is that the pressure-sensitive adhesive is applied in a different way and that the liquid-impermeable rear layer 13 can breathe. Such a breathable rear layer 13 can be SMS (spunbond-meltblown-spunbond) or a breathable plastic film consisting of, for example, polyethylene. This type of breathable film is described in, for example, EP 283 200. In order to retain its breathable quality when applied on a product, the lower side 11 may not be covered completely by the adhesive layer. The adhesive is therefore applied in three areas 15a, 15b and 15c. Strip 15a is laid along the longitudinal centre line 8 of the product and extends from the narrowest short side 5 over the whole length of the product. Adhesive strips 15b and 15c are arranged parallel with adhesive strip 15a, on each side of the longitudinal centre line 8, at a distance from the long sides in the first end portion 6. The adhesive strips 15a, 15b and 15c are about 10 mm wide positioned about 11 mm apart. Strip 15a is placed about 6 mm from each of the long sides 2 and 3. This is to provide more comfort for the wearer by reducing the risk of the adhesive sticking to the body hair. Strips 15b and 15c lie within the first, front end portion 6 of the product. Where the product is at its widest, the adhesive strips 15b, 15c do not reach as far as the side edges 2, 3 of the product, which they do where the product narrows closer to its transverse centre ine 9.

FIG. 6 shows an alternative embodiment of the protection for briefs where the long sides 2 and 3 have an undulated form, but are essentially arcuate.

FIG. 7 shows a part of an absorbent product according to the invention. The figure shows how it is possible to specify a favorable arc shape of the long sides 2 and 3 of the product in the second end portion 7. A line X running in the transverse direction of the article is drawn at a tangent to the short side 5 situated in the second end portion of the product. At a distance L=80 mm from line X, a line B is drawn parallel with X. It is those parts of the product lying between lines X and B which form basis for the measurement of the arc shape. Long side 2 intersects line B at point P. Side 2 stops curving away from longitudinal centre line 8 when it approaches the second short side 5. When itis very close thereto, e.g. less than a few millimeters, it curves towards longitudinal centre line 8. That point where the curvature changes direction is called Q. A line N is then drawn between points P and Q. The angle formed between lines X and N is called angle v. For a favorable curvature of long sides 2 and 3, v=95–110°.

The long side does not need to change curvature, but can run with the same direction of curvature down to its intersection with short side 5. This intersection then forms point Q. Short side 5 can be completely straight, and line X will then coincide with the short side.

The invention is not to be considered as being limited to the above-mentioned embodiments. They are intended only to clarify the invention.

Characteristics of various embodiments can be combined with one another within the scope of the invention. For example, the various adhesive patterns in the different embodiments can of course be combined with other alternative features of the other embodiments.

What is claimed is:

1. An absorbent product such as a sanitary towel, incontinence protection or protection for briefs, which product (1; 18) has an elongate shape with a longitudinal direction (8) and a transverse direction (9), an upper side (10) and a lower side (11), and has a first end portion (6) intended to face forwards on the wearer and a second end portion (7) intended to face backwards on the wearer, and wherein the first end portion (6) has greater width than the second end portion (7) and the width of the second end portion (7) of the product is 40 mm maximum, wherein the long sides (2, 3) of this end portion (7) are essentially arcuate and curved inwards towards the longitudinal centre line (8) of the product; the curvature of said long sides (2, 3) changes from concave to convex at a second point (Q) or with unchanged curvature direction intersects said end edge (5), and the angle (v) between an end line (X), which runs in the transverse direction of the product and tangent to the edge (5) of its second end portion (7), and a side line (N), drawn between a first point (P), which forms the intersection between one long side (2) of the product and a straight line (B) running in the transverse direction of the product at a distance of 80 mm from said end line (X), and said second point (Q) lies between 95° and 110°.

2. Absorbent product according to claim 1, characterised in that the width of the second end portion (7) is 20–40 mm.

3. Absorbent product according to claim 1, characterised in that the width of the second end portion (7) is 20–30 mm.

4. Absorbent product according to claim 2, characterized in that the length of the product (1; 18) is 150 mm or smaller.

5. Absorbent product according to claim 4, characterized in that the lower side (11) of the product is fitted with fastening means (15', 15a, 15b, 15c), which extend in a strip-shaped manner in the longitudinal direction of the product parallel with its longitudinal center line (8).

6. Absorbent product according to claim 1, characterized in that the length of the product (1; 18) is 150 mm or smaller.

7. Absorbent product according to claim 1, characterized in that the lower side (11) of the product is fitted with fastening means (15', 15a, 15b, 15c), which extend in a strip-shaped manner in the longitudinal direction of the product parallel with its longitudinal center line (8).

8. Absorbent product according to claim 7, characterised in that the product has three fastening strips, comprising a central fastening strip (15a), which extends along the longitudinal centre line (8) over essentially the entire length of the product, and two further fastening strips (15b, 15c) which are arranged one on each side thereof and at a distance therefrom and the extent of which lies within the first, front end portion (6) of the product.

* * * * *